(12) United States Patent
Uemori

(10) Patent No.: US 10,368,725 B2
(45) Date of Patent: Aug. 6, 2019

(54) ENDOSCOPE SYSTEM, IMAGE PROCESSING DEVICE, IMAGE PROCESSING METHOD, AND PROGRAM

(71) Applicant: SONY CORPORATION, Tokyo (JP)

(72) Inventor: Takeshi Uemori, Tokyo (JP)

(73) Assignee: SONY CORPORATION, Tokyo (JP)

( * ) Notice: Subject to any disclaimer, the term of this patent is extended or adjusted under 35 U.S.C. 154(b) by 227 days.

(21) Appl. No.: 15/327,062

(22) PCT Filed: Oct. 27, 2015

(86) PCT No.: PCT/JP2015/005379
§ 371 (c)(1),
(2) Date: Jan. 18, 2017

(87) PCT Pub. No.: WO2016/072059
PCT Pub. Date: May 12, 2016

(65) Prior Publication Data
US 2017/0135563 A1 May 18, 2017

(30) Foreign Application Priority Data

Nov. 6, 2014 (JP) ................................ 2014-226055

(51) Int. Cl.
| | |
|---|---|
| *A61B 1/00* | (2006.01) |
| *H04N 5/232* | (2006.01) |
| *H04N 5/353* | (2011.01) |
| *A61B 1/04* | (2006.01) |
| *H04N 5/225* | (2006.01) |

(52) U.S. Cl.
CPC ...... *A61B 1/00179* (2013.01); *A61B 1/00009* (2013.01); *A61B 1/00045* (2013.01); (Continued)

(58) Field of Classification Search
CPC ... A61B 1/00179; A61B 1/04; A61B 1/00045; A61B 1/00009; A61B 1/00174; (Continued)

(56) References Cited

U.S. PATENT DOCUMENTS

| | | |
|---|---|---|
| 2005/0154260 A1 | 7/2005 | Schara et al. |
| 2005/0250992 A1* | 11/2005 | Scherr .................. A61B 1/07 600/182 |

(Continued)

FOREIGN PATENT DOCUMENTS

| | | |
|---|---|---|
| EP | 2 664 272 A1 | 11/2013 |
| JP | 05-049599 A | 3/1993 |

(Continued)

OTHER PUBLICATIONS

Office Action dated Jan. 11, 2018 in Japanese Patent Application No. 2014-226055.

(Continued)

*Primary Examiner* — Allen C Wong
(74) *Attorney, Agent, or Firm* — Oblon, McClelland, Maier & Neustadt, L.L.P.

(57) ABSTRACT

Disclosed herein is an image processing device and method for image stabilization of an image signal input from an endoscope device including an objective lens provided at a distal end, the objective lens being disposed such that an optical axis of the objective lens and longitudinal axis of the objective lens intersect a predetermined angle, an endoscope head provided at a proximal end, and a gyro sensor provided on the endoscope head and to detect an angular velocity of movement of the endoscope head. The device includes circuitry configured to implement the image stabilization of the image signal input from the endoscope device based on the angular velocity of movement of the endoscope head of the endoscope device detected by the endoscope device.

15 Claims, 13 Drawing Sheets

(52) U.S. Cl.
CPC ............ *A61B 1/00174* (2013.01); *A61B 1/04* (2013.01); *H04N 5/23238* (2013.01); *H04N 5/23258* (2013.01); *H04N 5/23267* (2013.01); *H04N 5/3532* (2013.01); *H04N 2005/2255* (2013.01)

(58) Field of Classification Search
CPC ............ H04N 5/23238; H04N 5/3532; H04N 5/23258; H04N 5/23267; H04N 2005/2255
USPC ........................................................ 348/36
See application file for complete search history.

(56) References Cited

U.S. PATENT DOCUMENTS

| | | | |
|---|---|---|---|
| 2006/0106284 A1* | 5/2006 | Shouji | A61B 1/00009 600/118 |
| 2008/0159653 A1* | 7/2008 | Dunki-Jacobs | A61B 1/04 382/293 |
| 2011/0193948 A1* | 8/2011 | Amling | A61B 1/00006 348/68 |
| 2012/0262559 A1 | 10/2012 | On | |
| 2013/0194403 A1* | 8/2013 | Higuchi | H04N 5/23251 348/65 |
| 2013/0286174 A1 | 10/2013 | Urakabe | |

FOREIGN PATENT DOCUMENTS

| | | |
|---|---|---|
| JP | 2006-218129 A | 8/2006 |
| JP | 2009-254736 A | 11/2009 |

OTHER PUBLICATIONS

International Search Report dated Feb. 4, 2016 in corresponding PCT/JP2015/005379.

* cited by examiner

ENDOSCOPE SYSTEM, IMAGE PROCESSING DEVICE, IMAGE PROCESSING METHOD, AND PROGRAM

TECHNICAL FIELD

The present technology relates to an endoscope system, an image processing device, an image processing method, and a program, and more particularly to an endoscope system, an image processing device, an image processing method, and a program that allow implementing image stabilization even when a so-called oblique-view endoscope, among other endoscope devices used in an endoscopic surgery.

BACKGROUND ART

There has been disclosed, in the field of imaging devices such as a video camera, a technology which corrects a camera shake of an image by using a gyroscope provided on an imaging device for detecting a camera shake amount (see PTL 1).

The technology in PTL 1 describes correction of a camera shake by a shift of image data in a direction direct to an optical axis by ftanθ or fθ based on a shake amount detected by a sensor such as a gyroscope.

In the description, f is a focal distance of an imaging optical system, while θ is a rotation angle of the imaging device rotating around an axis direct to the optical axis, as an angle detected and calculated by the sensor such as a gyroscope.

CITATION LIST

Patent Literature

PTL 1: JP 2013-113962 A

SUMMARY OF INVENTION

Technical Problem

In general, a video camera images a target object present several meters to several tens of meters away. In this case, a distance between the optical system of the imaging device and the target object (hereinafter referred to as "subject distance") is sufficiently longer than a distance between a rotation center of rotation produced by a camera shake and the optical system of the imaging device (hereinafter referred to as "rotation radius").

According to the method described in PTL 1 or others, therefore, a shift amount for image stabilization is calculated on the assumption that the rotation radius is short enough to be in an ignorable level in comparison with the subject distance.

On the other hand, a rigid endoscope device images a target object present several millimeters to several centimeters away. In an endoscopic surgery, a rigid scope is inserted through a cylinder called a trocar, and introduced into the abdominal cavity.

In this case, the rigid scope rotates with a fulcrum located at the trocar. According to the rigid endoscope device, the rotation radius is not small enough to be in an ignorable level with respect to the subject distance, and therefore, the image stabilization method described in PTL 1 or others is not effective.

In addition, there is a rigid endoscope called an oblique-view scope, which includes a rigid scope whose optical axis is disposed obliquely to an axis of a barrel, in addition to an ordinary direct-view rigid endoscope. In a case of the oblique-view scope, image stabilization is effective only when a shift amount for image stabilization is calculated in consideration of an angle formed by the barrel axis of the oblique-view scope and the optical axis of the optical system, and a rotation angle of the barrel from a reference position, as well as the subject distance and the rotation radius.

The present technology has been developed in the light of the aforementioned circumstances. The present technology implements image stabilization in consideration of a subject distance, a rotation radius, an angle formed by a barrel axis of an oblique-view scope and an optical axis of an optical system, and a rotation angle of the oblique-view scope from a reference position.

Solution to Problem

An endoscope system according to one aspect of the present disclosure is an endoscope system that includes an endoscope device that includes an objective lens provided at a distal end, the objective lens being disposed such that an optical axis of the objective lens and a longitudinal axis of the objective lens intersect at a predetermined angle, an endoscope head provided at a proximal end, and a gyro sensor provided on the endoscope head and to detect an angular velocity of movement of the endoscope head and image processing circuitry configured to implement image stabilization of an image signal input from the endoscope device based on the detected angular velocity.

An image processing device according to one aspect of the present disclosure includes is an image processing device for image stabilization of an image signal input from an endoscope device including an objective lens provided at a distal end, the objective lens being disposed such that an optical axis of the objective lens and longitudinal axis of the objective lens intersect a predetermined angle, an endoscope head provided at a proximal end, and a gyro sensor provided on the endoscope head and to detect an angular velocity of movement of the endoscope head. The device includes circuitry configured to implement the image stabilization of the image signal input from the endoscope device based on the angular velocity of movement of the endoscope head of the endoscope device detected by the endoscope device.

An image processing method according to one aspect of the present disclosure is an image processing method implemented by image processing circuitry configured to process an image signal input from an endoscope device, the endoscope device including an objective lens provided at a distal end, the objective lens being disposed such that an optical axis of the objective lens and longitudinal axis of the objective lens intersect at a predetermined angle, an endoscope head provided at a proximal end, and a gyro sensor provided on the endoscope head and to detect an angular velocity of movement of the endoscope head. The method includes the step of implementing image stabilization of the image signal based on the detected angular velocity of movement of the endoscope head of the endoscope device.

A medium according to one aspect of the present disclosure is a non-transitory computer readable medium having stored thereon a program which when executed by a computer causes the computer to implement a method implemented by image processing circuitry configured to process an image signal input from an endoscope device, the endoscope device including an objective lens provided at a distal end, the objective lens being disposed such that an optical axis of the objective lens and longitudinal axis of the objective lens intersect at a predetermined angle, an endoscope head provided at a proximal end, and a gyro sensor provided on the endoscope head and to detect an angular velocity of movement of the endoscope head. The method includes the step of implementing image stabilization of the image signal based on the detected angular velocity of movement of the endoscope head of the endoscope device.

The endoscope system and the image processing device according to the one aspect of the present technology may be either independent devices, or included in a block functioning as both the endoscope system and the image processing device.

Advantageous Effects of Invention

According to the one aspect of the present technology, image stabilization is achievable in consideration of a subject distance, a rotation radius, an angle formed by a barrel axis of an oblique-view scope and an optical axis of an optical system, and a rotation angle of the oblique-view scope from a reference position.

DESCRIPTION OF EMBODIMENTS

A best mode for carrying out the present technology (hereinafter referred to as embodiment) is hereinafter described in detail with reference to the drawings.

<Outline of Endoscope System>

Figure 1:
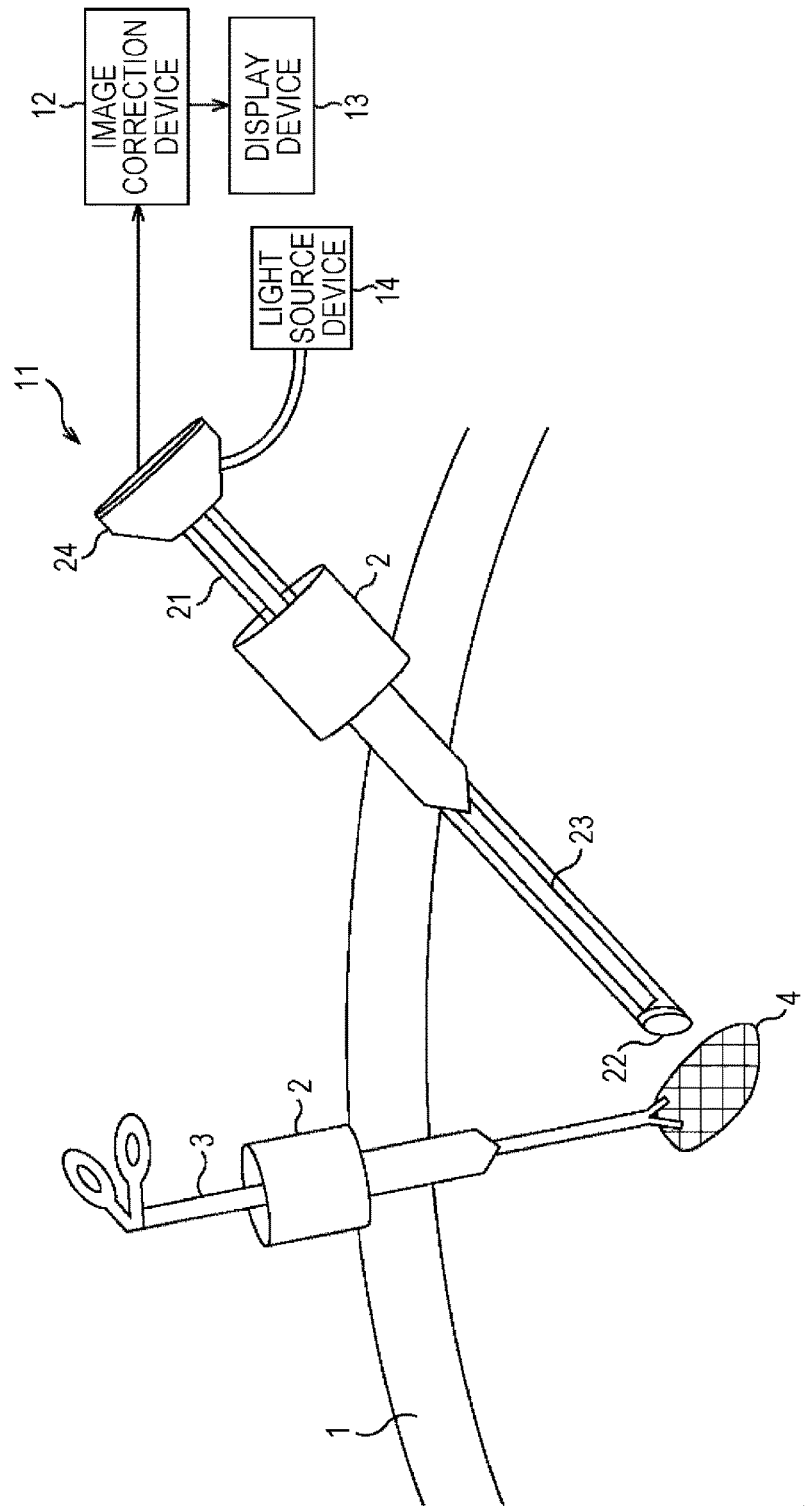
FIG. 1 is a view illustrating an outline of a laparoscopic surgery.

FIG. 1 is a view illustrating an outline of an endoscope system to which the present technology has been applied.

This endoscope system is used in a laparoscopic surgery conducted in recent years in the medical practice, in place of a conventional open abdominal surgery.

More specifically, in case of a laparoscopic surgery in an abdominal region, for example, opening tools called trocars 2 are attached to several points of an abdominal wall as illustrated in FIG. 1. In this condition, a laparoscope (hereinafter also referred to as "endoscope device" or "endoscope") 21, and a treatment device 3 are inserted through holes formed in the trocars 2 and introduced into the body, instead of cutting the abdominal wall 1 as in the conventional open abdominal surgery. Then, treatments such as cutting off a diseased part (such as tumor) 5 by using the treatment device 4 are performed with a real-time view of a video image of the diseased part 4 captured by an endoscope device 11.

In a case of video image captured by the endoscope device 11, an image shake may be produced in an obtained image, and therefore, a mechanism for correcting the image shake is necessary.

According to the linear bar-shaped endoscope device 11 illustrated in FIG. 1, a head unit 24 is held by an operator, an assistant, a scopist, a robot, or the like. When the hand or the like holding the head unit 24 shakes, motion of this shake is conducted to an objective lens 22 with a fulcrum (rotation center) located at the trocar 2. Accordingly, an image shake may be produced as a result of the shake of the hand holding the head unit 24.

The endoscope system according to an embodiment of the present technology is a system capable of implementing so-called image stabilization for correcting image distortion produced by an image shake.

<Configuration Example of Endoscope System>

A configuration example of the endoscope system according to an embodiment of the present technology is hereinafter described with referent to FIG. 2. An endoscope system 10 according to the present embodiment includes the endoscope device 11, an image correction device (image processing device) 12, and a display device 13.

The endoscope device 11 and the image correction device 12 may be connected with each other not only via a cable but also by radio. The image correction device 12 may be placed at a position away from an operating room and connected via a network such as a premises LAN or the Internet. This structure is applicable to connection between the image correction device 12 and the display device 13.

The endoscope device 11 includes a linear bar-shaped barrel unit 21, and the head unit 24. The barrel unit 21 is called a telescopic tube or rigid tube as well, and is approximately several tens of centimeters in length. The objective lens 22 is provided at one end of the barrel unit 21 on the side inserted into the body, while the other end is connected with the head unit 24. An optical lens unit 23 of a relay optical system is housed within the barrel unit 21. The shape of the barrel unit 21 is not limited to the linear bar shape.

The endoscope system can be arranged such that the barrel unit (endoscope device) and head unit (endoscope head) are detachable, and information of the barrel unit (e.g. type of the scope (direct-view scope/oblique-view scope) and oblique view angle) can be sent to the head unit by contact or contactless transmission there-between. In this case, the lens barrel unit includes memory that stores basic information of the lens barrel (e.g. type of endoscope, oblique view angle, diameter of the scope and focus range, etc.)

Figure 2:
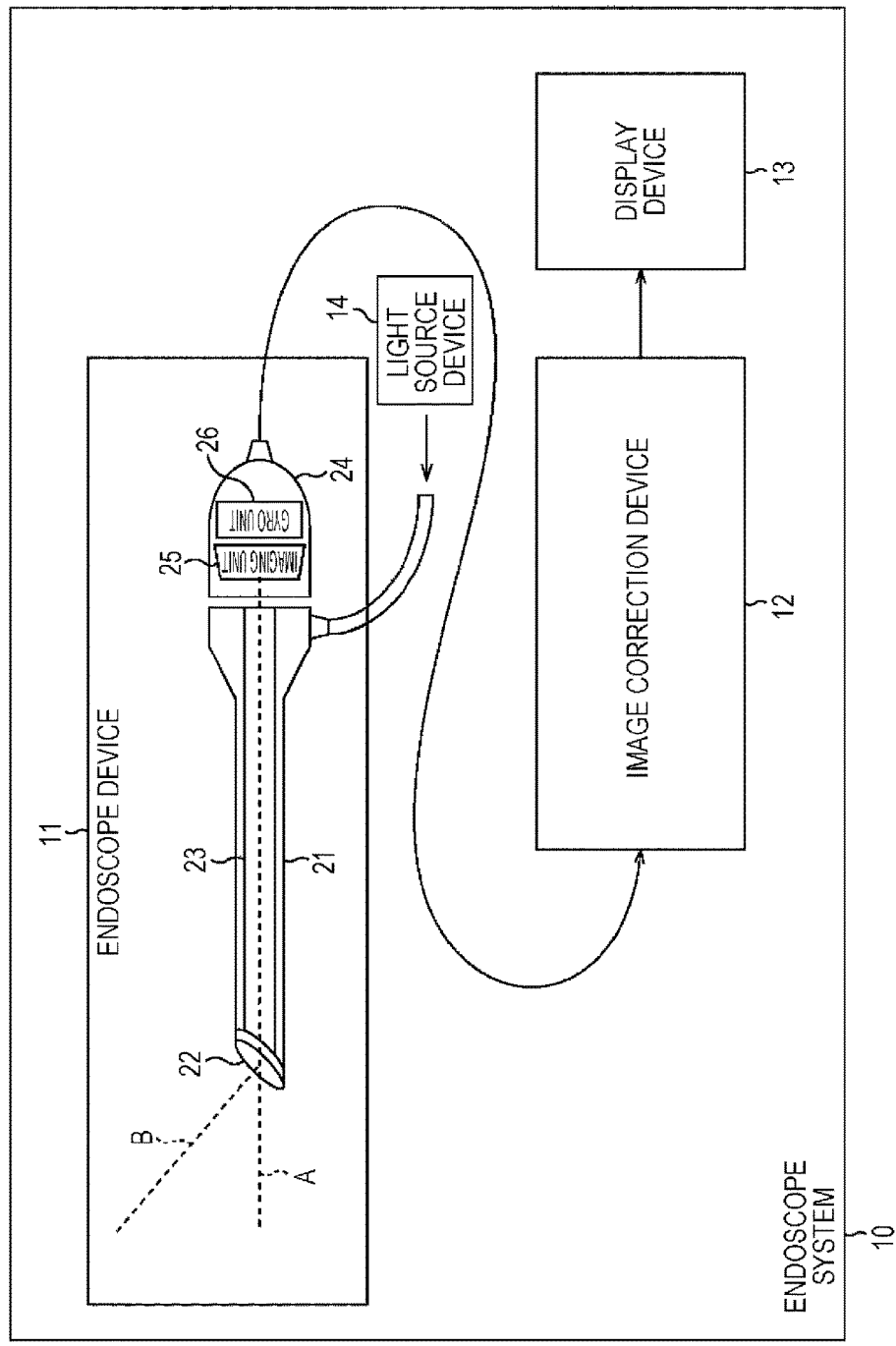
FIG. 2 is a block diagram illustrating a configuration example of an endoscope system to which the present disclosure has been applied.

The types of the barrel unit 21 are roughly divided into: a direct-view scope type in which barrel axis A and optical axis B illustrated in FIG. 2 agree with each other; and an oblique-view scope type in which barrel axis A and optical axis B form a predetermined angle. The barrel unit 21 illustrated in FIG. 2 is an example of the oblique-view scope of the two types. In the oblique-view scope, the predetermined angle formed by the barrel axis A and the optical axis B is called an oblique-view angle as well, and generally set to 30 degrees or 70 degrees, for example. However, oblique-view scopes having other angles are present and available to allow arbitrary setting of the oblique-view angle.

The head unit 24 accommodates an imaging unit 25 and a gyro unit 26. The imaging unit 25 contains an image sensor such as CMOS (Complementary Metal Oxide Semiconductor), and converts an optical image of the diseased part input from the barrel unit 21 into an image signal having a predetermined frame rate. The head unit 24 further connects with a light source device 14, and receives supply of a light source necessary for imaging from the light source device 14 to illuminate the diseased part 4 via the optical lens unit 23. In this case, the light source device 14 is capable of emitting lights having a variety of wavelengths as switchable lights, and also generating special light for specifically identifying the diseased part 4 in addition to ordinary light. Accordingly, the imaging unit 25 is capable of generating an image from an image signal of special light as well as an image signal of ordinary light.

The gyro unit 26 detects an angular velocity of movement of the head unit 24, and outputs the detection result to the subsequent image correction device 12.

According to the endoscope device 11, an optical image of the diseased part, where light is concentrated by the objective lens 22, enters the imaging unit 25 of the head unit 24 via the optical lens unit 23. The optical image having entered the imaging unit 25 is converted into an image signal having the predetermined frame rate, and output to the subsequent image correction device 12. In addition, according to the endoscope device 11, the angular velocity of the movement of the head unit 24 is detected by the gyro unit 26, and output to the subsequent image correction device 12.

Figure 3:
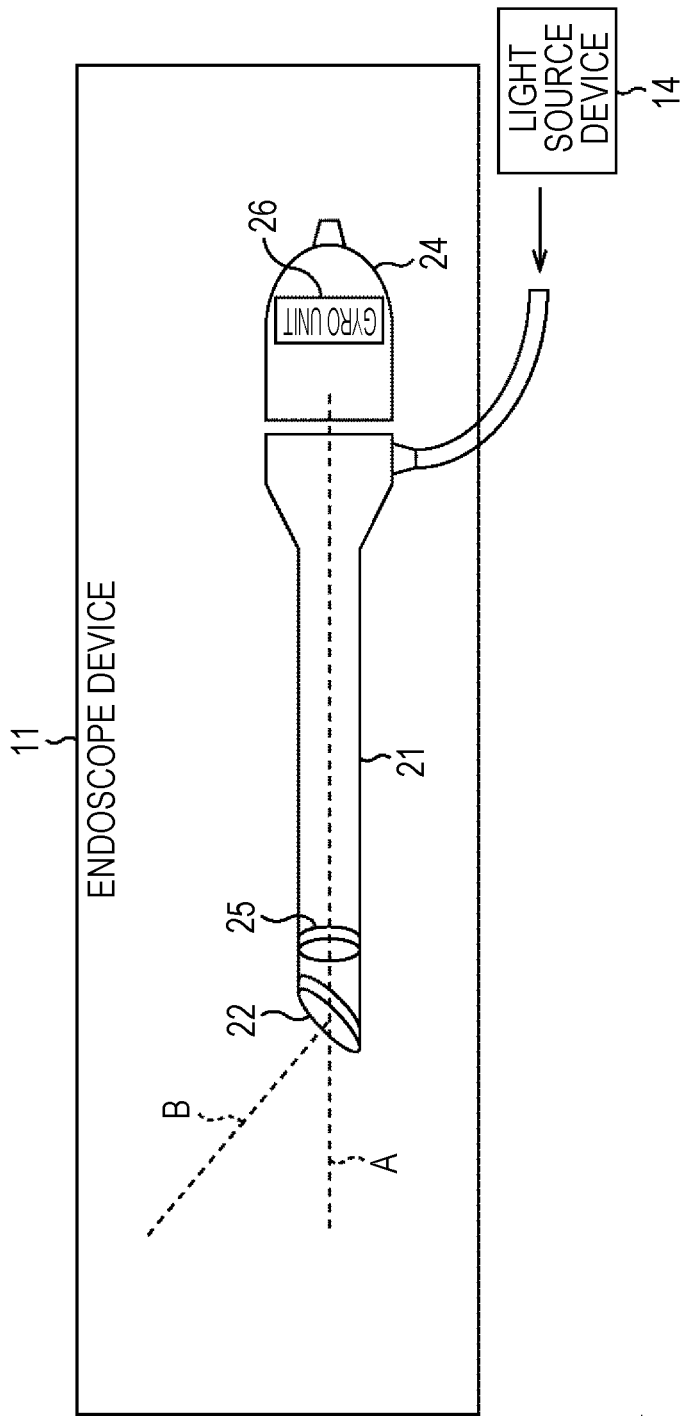
FIG. 3 is a block diagram illustrating another configuration example of the endoscope device illustrated in FIG. 2.

FIG. 3 illustrates another configuration example of the endoscope device 11. As illustrated in this figure, the imaging unit 25 may be disposed immediately behind the objective lens 22 to eliminate the optical lens unit 23 within the barrel unit 21.

<Outline of Correction Process>

Figure 4:
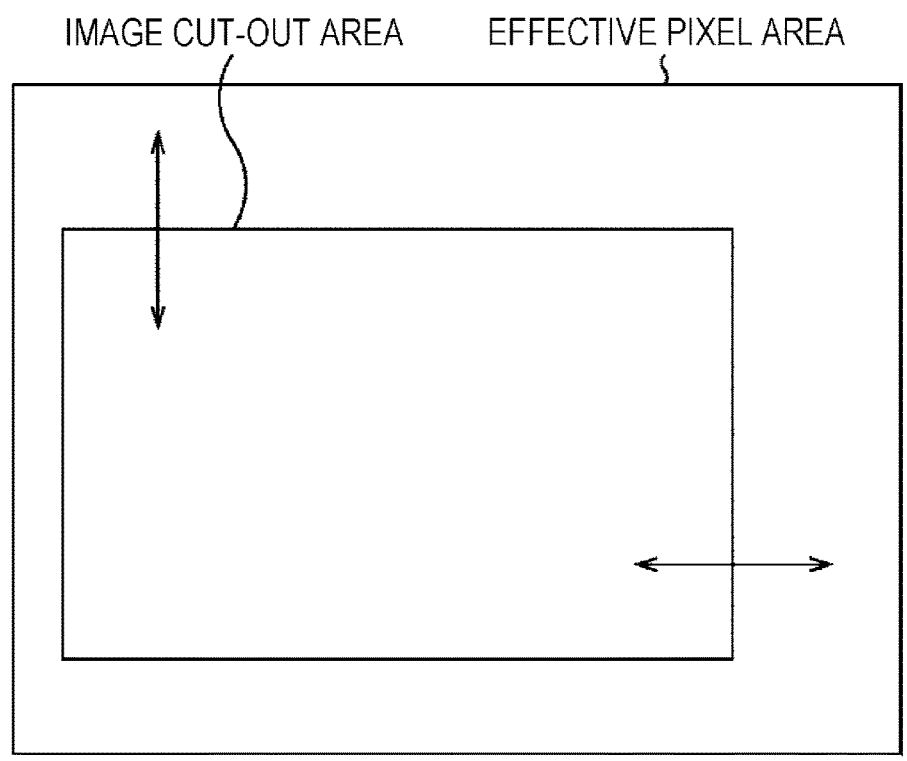
FIG. 4 is a view illustrating an outline of a correction process performed by a figure image correction device.

An outline of a correction process performed by the image correction device 12 is hereinafter described with reference to FIG. 4. The image correction device 12 cuts out an area from the entire area of an image signal (effective pixel area) having a predetermined frame rate and input from the imaging unit 25 of the endoscope device 11 as a cut-out area in a size smaller than the effective pixel area, and outputs an image signal generated based on the cut-out area to the subsequent display device 13. During this process, a camera shake is correctable by shifting the position of the cut-out area by a shift amount corresponding to the camera shake. In addition, when a rolling shutter is provided as a shutter mechanism of the imaging unit 25 of the endoscope device 11, rolling shutter distortion produced by the configuration can be removable.

<Configuration Example of Image Correction Processing Device>

Figure 5:
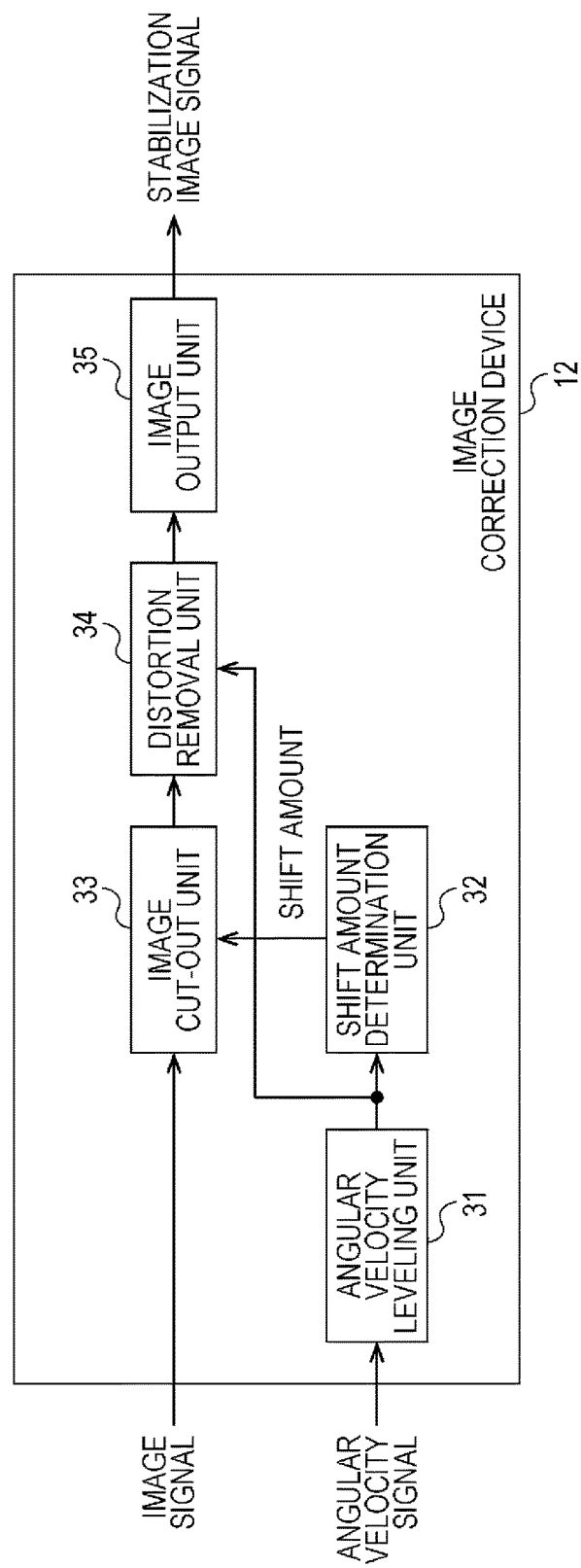
FIG. 5 is a block diagram illustrating a configuration example of the image correction device.

A configuration example of the image correction device 12 is hereinafter described with reference to FIG. 5. The image correction device 12 includes an angular velocity leveling unit 31, a shift amount determination unit 32, an image cut-out unit 33, a distortion removal unit 34, and an image output unit 35.

The angular velocity leveling unit 31 levels angular velocities of the head unit 24 detected by the gyro unit 26 of the endoscope device 11, based on integration of the angular velocities in a time direction. Thereafter, the angular velocity leveling unit 31 removes instantaneous errors from the leveled angular velocity, and outputs the resultant angular velocity to the shift amount determination unit 32 and the distortion removal unit 34.

The shift amount determination unit 32 calculates a shift amount of the objective lens 22 based on the leveled angular velocity, determines a shift amount of an image cut-out area based on the shift amount of the calculated objective lens 22, and notifies the image cut-out unit 33 of the shift amount of the image cut-out area. The shift amount of the image cut-out area corresponding to the shift amount of the objective lens 22 varies in accordance with magnification of the objective lens 22. Accordingly, the shift amount determination unit 32 retains a function for calculating the shift amount based on the magnification and shift amount of the objective lens 22, or retains a table showing the respective correspondences beforehand.

The image cut-out unit 33 cuts out pixels of the cut-out area from the image signal having the predetermined frame rate and sequentially input from the imaging unit 25 of the endoscope device 11. The position of the cut-out area is adjusted in accordance with the shift amount obtained from the shift amount determination unit 32. The image cut-out unit 33 generates a stabilization image signal based on the cut-out area, and outputs the stabilization image signal to the distortion removal unit 34.

The distortion removal unit 34 removes rolling shutter distortion (possibly produced when a rolling shutter is provided as the shutter mechanism of the imaging unit 25) from the stabilization image signal received from the image cut-out unit 33, if any, and outputs the resultant stabilization image signal to the image output unit 35. Rolling shutter distortion may be removed by using an existing arbitrary method.

The image output unit 35 outputs the stabilization image signal received from the distortion removal unit 34 to the subsequent unit (display device 13 in this case).

<Shift Amount Determination Method>

A method for determining the shift amount is hereinafter described.

Figure 6:
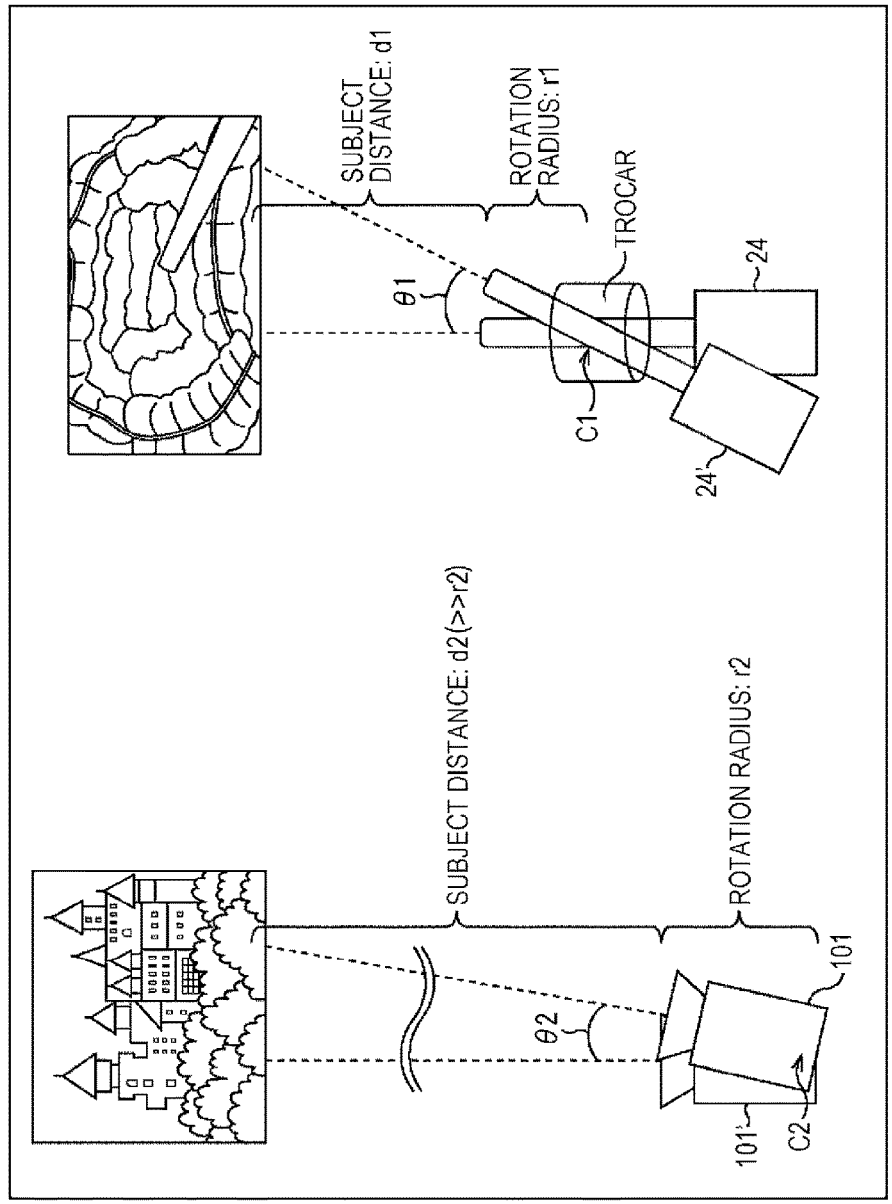
FIG. 6 is a view illustrating differences in image stabilization between a video camera and an endoscope device.

In general, a video camera images a target object present several meters to several tens of meters away, as illustrated in the left part of FIG. 6. In this case, a distance between an optical system of an imaging device 101 and the target object (hereinafter referred to as "subject distance") d2 is sufficiently longer than a distance between a rotation center c2 of rotation produced by a camera shake and the optical system of the imaging device 101 (hereinafter referred to as "rotation radius"). Accordingly, the method described in PTL 1 or others calculates a shift amount for image stabilization on the assumption that a rotation radius r2 is short enough to be in an ignorable level in comparison with the subject distance d2. The left part of FIG. 6 illustrates the imaging device 101 at a position when an imaging device 101' is shifted by a camera shake by a deviation angle θ2 around the rotation center c2.

On the other hand, an endoscope device images a target object at a subject distance d1 of several millimeters to several centimeters, as illustrated in the right part of FIG. 6. In case of a laparoscopic surgery, the endoscope device 11 is inserted through a cylinder called the trocar 2, and introduced into the abdominal cavity. In this case, the endoscope device 11 rotates with a fulcrum c1 located at the trocar 2. In a case of the endoscope device 11, a rotation radius r1 is not short enough to be in an ignorable level with respect to the subject distance d1, and therefore, the image stabilization method described in PTL 1 or the like is not effective. The right part of FIG. 6 illustrates a head unit 24' of the endoscope device 11 at a position when the head unit 24 is shifted by a camera shake by a deviation angle θ1 around the rotation center c1.

In a case of an oblique-view scope such as the endoscope device 11 employed in the present embodiment, image stabilization is effective only when the shift amount is calculated in consideration of an angle formed by a barrel axis of the oblique-view scope and the optical axis of the optical system, and a rotation angle of the barrel from a reference position, as well as the subject distance and the rotation radius.

Accordingly, a shift amount of a pinhole camera model is initially discussed herein as an example of the shift amount of the oblique-view scope so as to describe the shift amount of the oblique-view scope type endoscope device 11.

Figure 7:
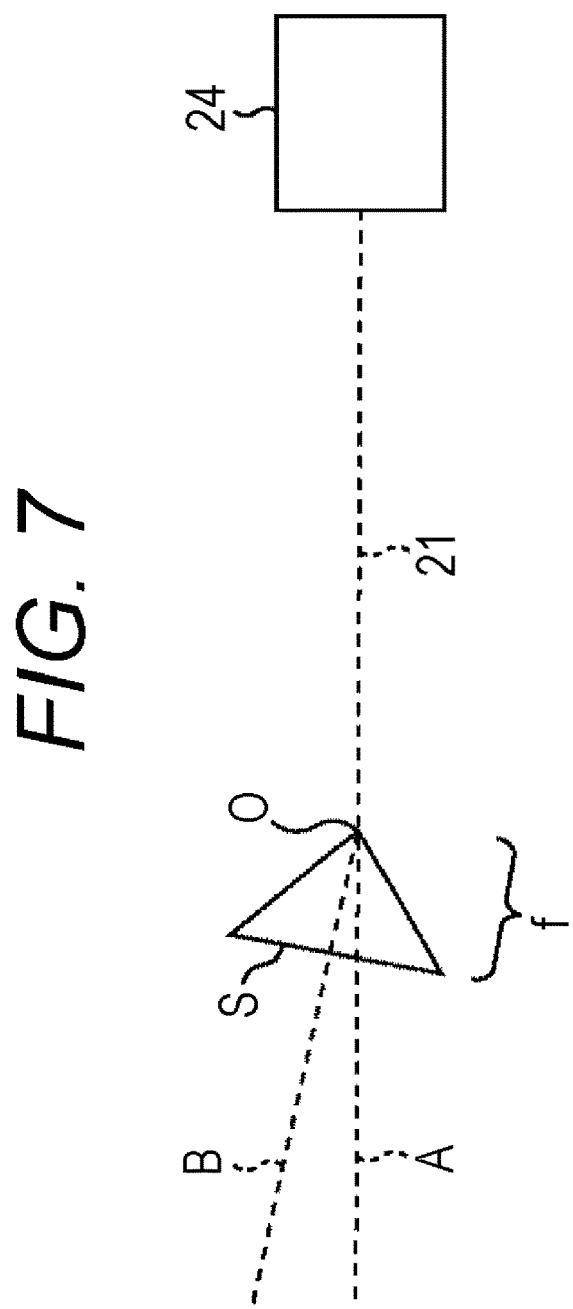
FIG. 7 is a view illustrating a configuration of an oblique-view scope using a pinhole camera model.

For example, according to the pinhole camera model illustrated in FIG. 7, a point O corresponds to an optical center (pinhole) on which light is concentrated. In this condition, an image (picture) is formed on an image surface S. In the actual configuration of the endoscope device 11, the imaging unit 25 is included in the head unit 24. However, for simplifying the explanation, it is considered herein that the image surface S is positioned in front the optical center O in FIG. 7. Herein, the distance between the optical center O and the image surface S is regarded as a focal distance f.

Figure 8:
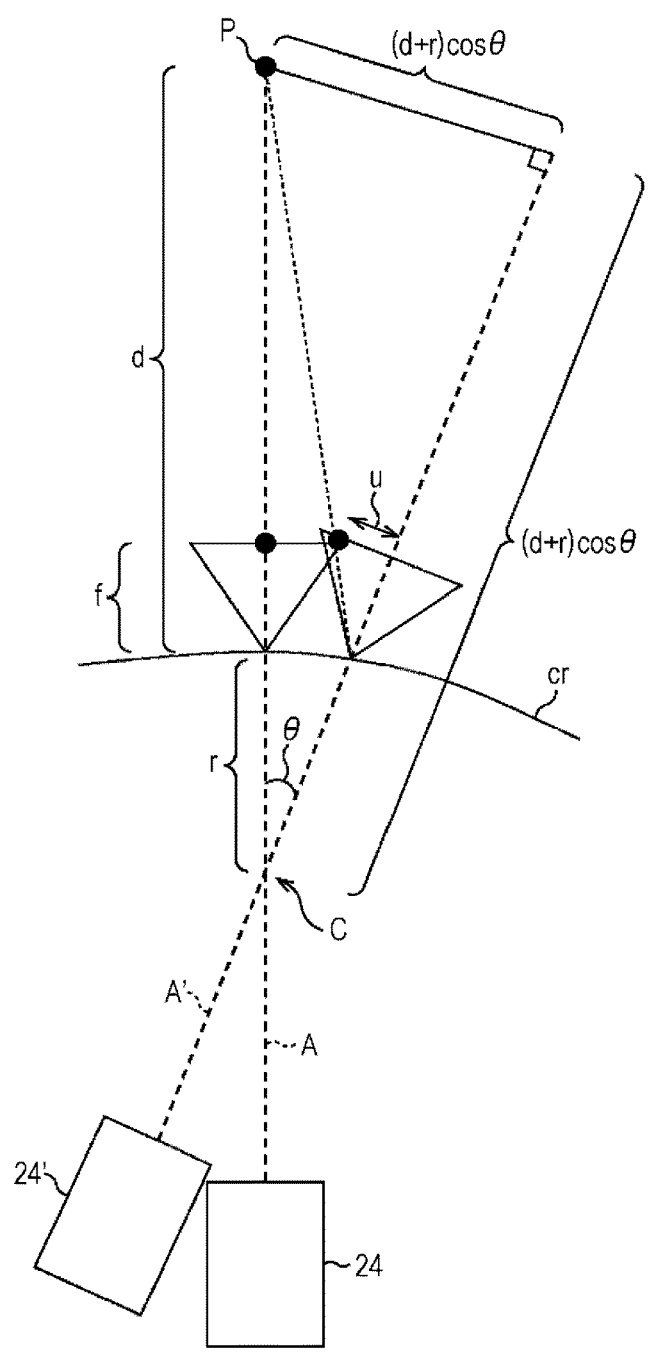
FIG. 8 is a view illustrating image stabilization by a direct-view scope.

Discussed next with reference to FIG. 8 is a method for calculating a shift amount for image stabilization in consideration of the subject distance and the rotation radius at the time of use of a direct-view scope whose barrel axis A and optical axis B agree with each other.

It is assumed that a point light source P corresponding to a subject is reflected at the center of the image surface of the imaging unit 25 included in the head unit 24 at a time t−1. It is also assumed that the head unit 24 shifts to the position of the head unit 24' rotated (shaken) by θ [radian] around a center point C during a period from the time t−1 to a time t. It is determined in this condition where the point light source P is reflected on an image surface of the head unit 24' at the time t. More specifically, a distance u between the position of the point light source on an image obtained by the head unit 24' at the time t, and the center of the image corresponds to the shift amount for image stabilization desired to be calculated. The shift amount u for image stabilization is defined by following Equation (1) based on a geometrical relationship illustrated in FIG. 8.

[Math. 1]

$$u = \frac{(d+r)\sin\theta}{(d+r)\cos\theta - r} f \quad (1)$$

In this equation, d indicates the subject distance, r indicates the rotation radius, and f indicates the focal distance. In general, a camera shake amount (rotation angle θ) during a micro time (one frame) is extremely short, and therefore, approximations of sin θ≈tan θ≈θ and cos θ≈1 are allowed. Accordingly, Equation (1) may be approximated as following Equation (2).

[Math. 2]

$$u = \frac{d+r}{d} f \tan\theta = \frac{d+r}{d} f\theta \quad (2)$$

In addition, when the rotation radius r is short enough to be in an ignorable level in comparison with the subject distance d (d≫r) in Equation (2), an approximation of d+r≈d is allowed. Accordingly, Equation (2) may be approximated as following Equation (3).

[Math. 3]

$$u = f\tan\theta = f\theta \quad (3)$$

The shift amount for image stabilization shown in this equation is equivalent to the shift amount for image stabilization of an ordinary imaging device such as a video camera described in PTL 1 or others.

In the case of the endoscope device 11, the rotation radius r is not ignorable with respect to the subject distance d as illustrated in FIG. 6. Accordingly, Equation (2) considering the rotation radius r and the subject distance d is used for implementing more effective image stabilization than that of the conventional method.

Discussed next is the case of an oblique-view scope including a rigid scope whose optical axis A is oblique to the axis B of the barrel.

Figure 9:
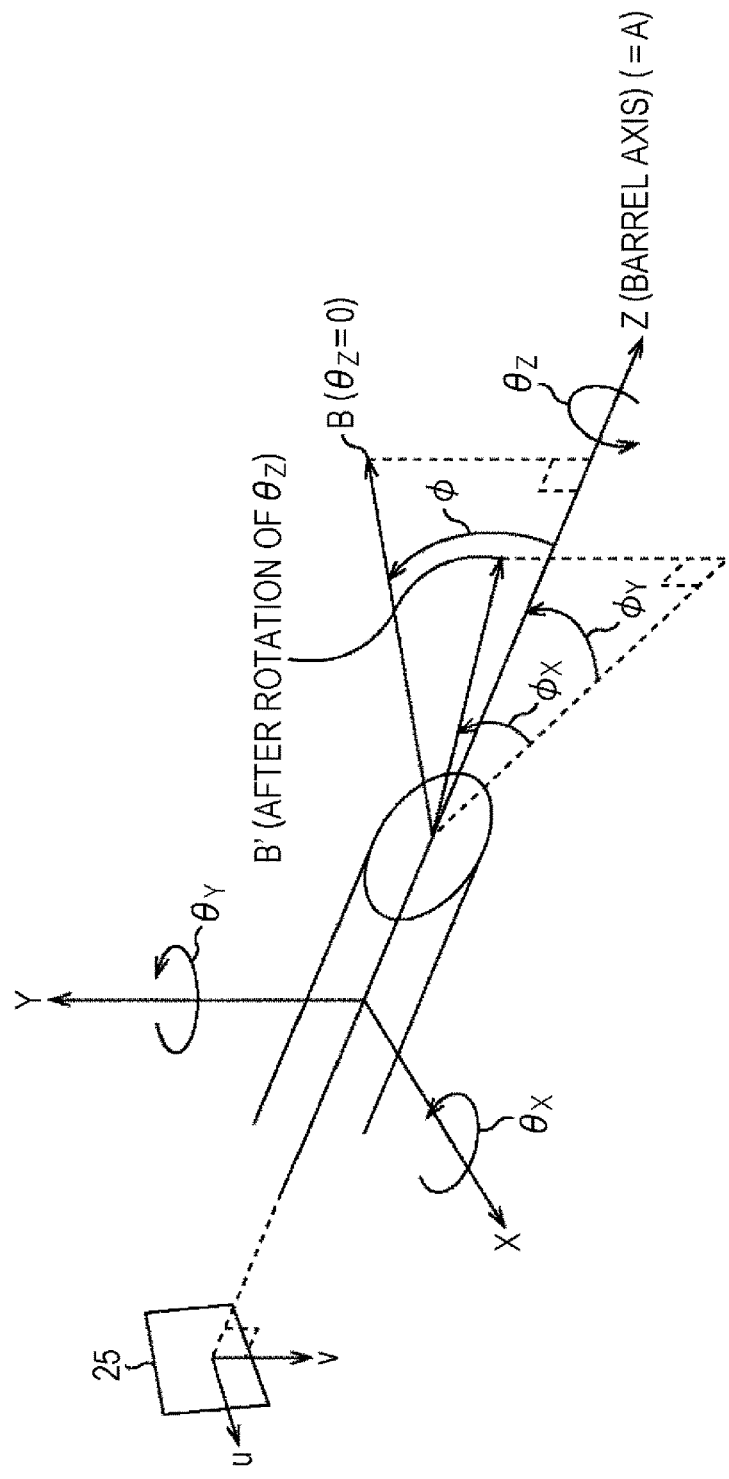
FIG. 9 is a view illustrating a camera shake direction of an oblique-view scope.

Parameters appearing in the following description are initially touched upon with reference to FIG. 9. In FIG. 9, an angle formed by the optical axis B of the oblique-view scope and the barrel axis (Z axis (=A)) is regarded as Φ [radian] when the oblique-view scope is located at a reference position (θz=0). An angle formed by the barrel axis Z of the oblique-view scope and a line of an optical axis B' of the oblique-view scope projected on the X-Z plane is regarded as Φy after the oblique-view scope is rotated from the reference position by θz. An angle formed by the optical axis of the oblique-view scope and the line of the optical axis of the oblique-view scope projected on the X-Z plane is regarded as Φx after the oblique-view scope is rotated from the reference position by θz. Rotation of the endoscope device 11 around the X axis is regarded as θx, and rotation of the endoscope device 11 around the Y axis is regarded as θy.

In this case, Φx and Φy as angular components of Φ in the X axis direction and the Y axis direction, respectively, are expressed, using Φ and θz, as following Equation (4) and Equation (5).

[Math. 4]

$$\phi_x = \tan^{-1}\left(\frac{\sin\phi\cos\theta_Z}{\cos\phi}\right) \quad (4)$$

[Math. 5]

$$\phi_y = \tan^{-1}\left(\frac{-\sin\phi\sin\theta_Z}{\cos\phi}\right) \quad (5)$$

Discussed next is the shift amount u for image stabilization in the horizontal direction of the imaging unit 25 included in the head unit 24 with reference to FIG. 10.

Figure 10:
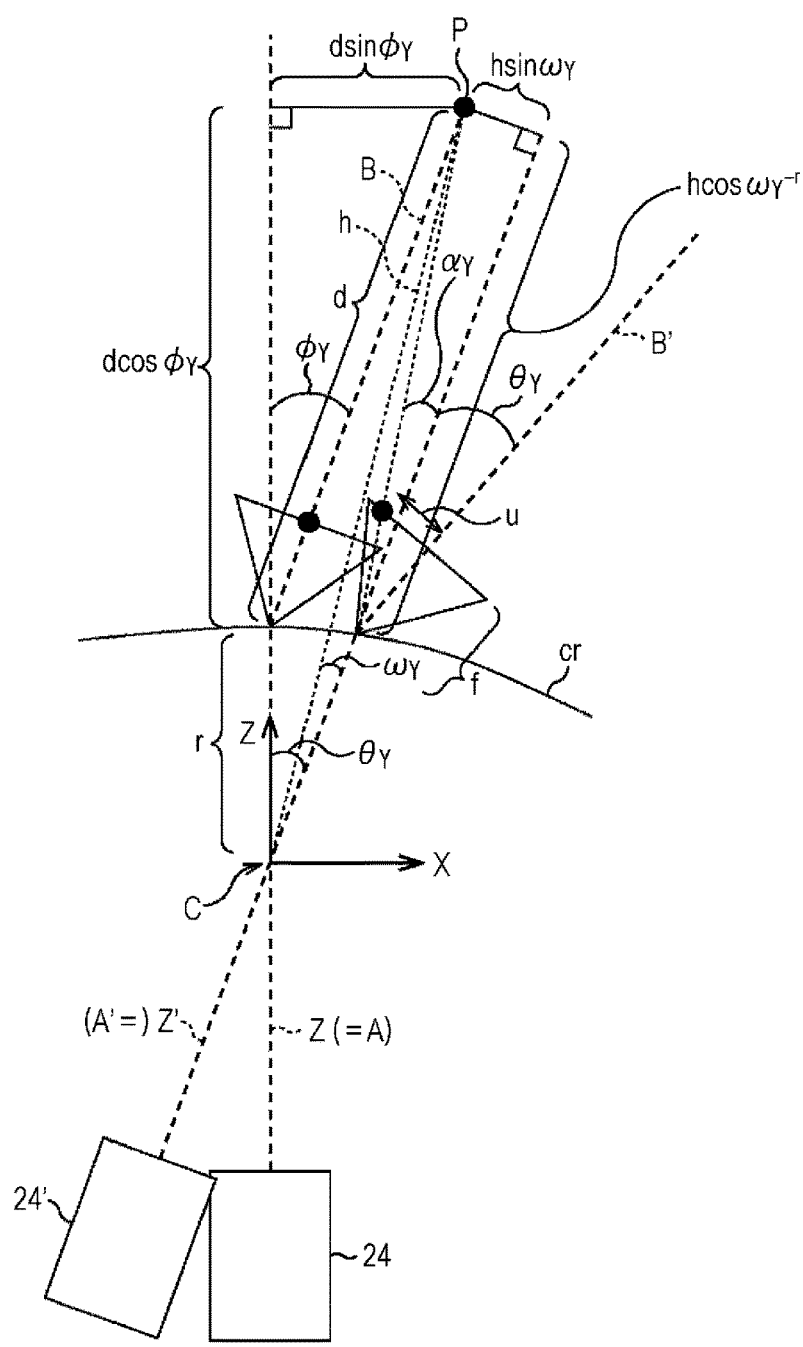
FIG. 10 is a view illustrating image stabilization by an oblique-view scope.

In FIG. 10, it is assumed that the head unit 24 is rotated by θz from the reference position. In this case, the angle Φy formed by the barrel axis Z (=A) and the line of the optical axis B projected on the X-Z plane is expressed as Equation (5). It is assumed herein that the point light source P corresponding to the subject is reflected at the center of the image surface of the imaging unit 25 included in the head unit 24 at the time t−1. It is also assumed that the head unit 24 is rotated (shaken) by θy [radian] around the Y axis with the center located at the rotation center C during the period from the time t−1 to the time t. It is determined in this condition where the point light source P is reflected on the image surface of the imaging unit 25 at the time t. More specifically, the distance u between the position of the point light source P on an image obtained by the imaging unit 25 at the time t and the center of this image corresponds to the shift amount to be used for image stabilization. In FIG. 10, r indicates the rotation radius, d indicates the subject distance between the optical center of the camera and the point light source P at the time t−1, and f indicates the focal distance.

As can be understood from the geometrical relationship illustrated in FIG. 10, the shift amount u for image stabilization is expressed by following Equation (6).

[Math. 6]

$$u = f \tan\theta(\phi_y + \alpha_y) \quad (6)$$

In this equation, αy indicates an angle formed by the barrel axis Z and a line connecting the point light source P and the optical center of the head unit 24 at the time t, and is defined by following Equation (7).

[Math. 7]

$$\alpha_y = \tan^{-1}\left(\frac{h\sin\omega_y}{h\cos\omega_y - r}\right) \quad (7)$$

In this equation, h indicates a line connecting the point light source P and the rotation center C. The length of h is defined by following Equation (8).

[Math. 8]

$$h = \sqrt{d^2 + r^2 + 2dr\cos\phi_y} \quad (8)$$

In Equation (7), ωy indicates an angle formed by the line h and the barrel axis Z at the time t, and is defined by following Equation (9).

[Math. 9]

$$\omega_y = \theta_y - \tan^{-1}\left(\frac{d\sin\phi_y}{r + d\cos\phi_y}\right) \quad (9)$$

Accordingly, the shift amount for image stabilization in consideration of the direction of the optical axis of the oblique-view scope is defined by Equation (6) noted above.

A shift amount v for image stabilization in the vertical direction of the imaging unit 25 is defined in a completely similar manner.

In a case of the direct-view scope, the angle Φ formed by the optical axis and the barrel axis is 0, and therefore, Φy=0 holds in Equation (5). Accordingly, when Φy=0 is substituted into Equation (6), Equation (6) becomes equivalent to Equation (3) used for calculating the shift amount for image stabilization in case of the direct-view scope.

The angle θy in Equation (6) produced by a camera shake, which is an angle of rotation around the Y axis with the rotation center located at the rotation center C, is detected by the gyro unit 26.

The subject distance d in Equation (6) may be given manually, or may be obtained by image analysis performed by the imaging unit 25 when the imaging unit 25 is configured to function as a distance sensor for detecting distances by using a time-of-flight method, for example.

The rotation radius r in Equation (6) may be given manually, or may be obtained by a sensor (such as a pressure sensor) attached to the imaging unit 25 or the trocar 2 or by image analysis, for example.

The angle formed by the optical axis of the rigid scope and the barrel axis (oblique-view angle) Φ in Equation (6) may be given manually, or may be obtained by image analysis, for example.

The Φ oblique view angle may be sent from the lens barrel to the head by contact or contactless transmission there-between.

The rotation angle θz of the endoscope device 11 from a reference value in Equation (6) may be given manually, or may be obtained by an angle detection sensor or by image analysis, for example.

<Description of Operation>

Figure 11:
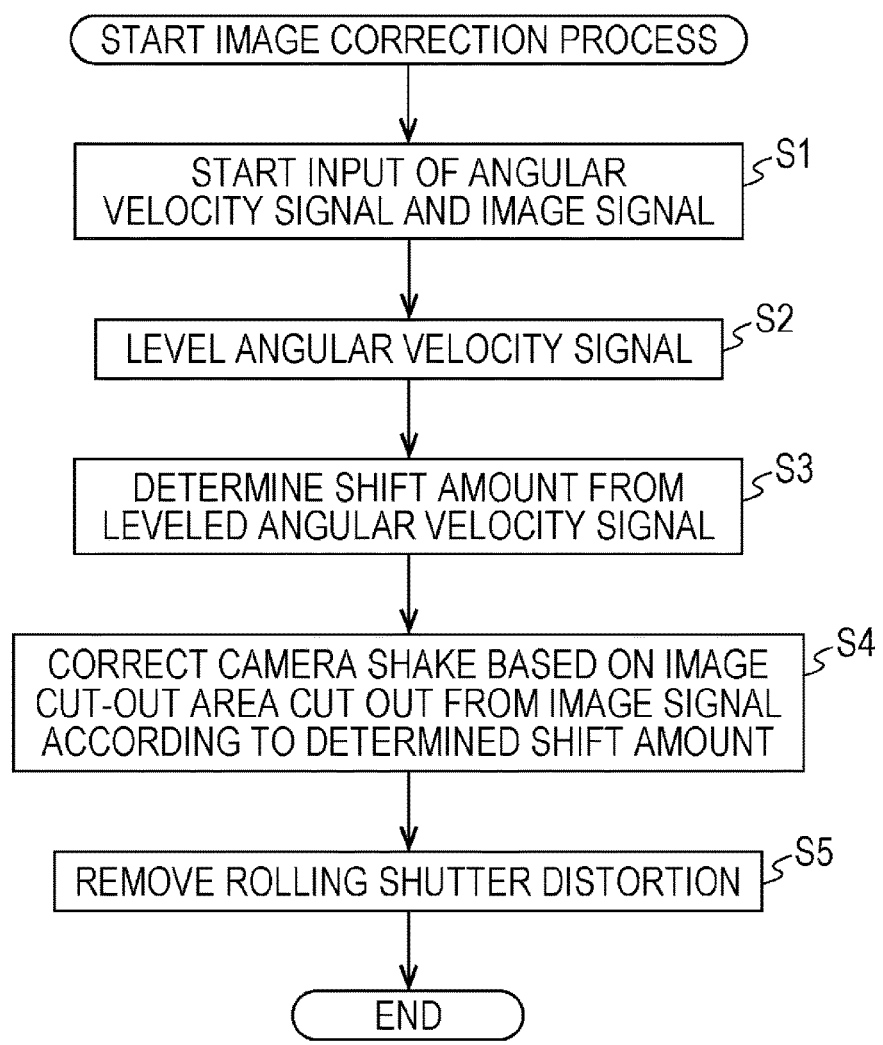
FIG. 11 is a flowchart showing an image correction process.

The image correction process performed by the image correction device 12 is hereinafter described with reference to a flowchart shown in FIG. 11. It is assumed herein that each of the subject distance d, the rotation radius r, and the angle Φ has been set beforehand by manual input, image analysis, or other methods, during calibration or other processing. The rotation angle θz is a value measured by the gyro unit 26.

In step S1, inputs of an image signal having a predetermined frame rate and an angular velocity signal indicating movement of the head unit 24 are started from the endoscope device 11 to the image correction device 12. The image signal is input to the image cut-out unit 33, while the angular velocity signal is input to the angular velocity leveling unit 31.

In step S2, the angular velocity leveling unit 31 integrates angular velocities of the head unit 24 detected by the gyro unit 26 of the endoscope device 11 in the time direction in order to level the angular velocities, and outputs the leveled angular velocity to the shift amount determination unit 32 and the distortion removal unit 34.

In step S3, the shift amount determination unit 32 calculates a shift amount of the objective lens 22 based on the leveled angular velocity by using Equation (6) noted above, determines the shift amount of an image cut-out area based on the calculated shift amount of the objective lens 22, and notifies the image cut-out unit 33 of the shift amount of the image cut-out area.

In step S4, the image cut-out unit 33 cuts out pixels of the cut-out area from the image signal having the predetermined frame rate and sequentially input from the endoscope device 11, while adjusting the position of the cut-out area in accordance with the shift amount received from the shift amount determination unit 32. The image cut-out unit 33 generates a stabilization image signal based on the cut-out area, and outputs the stabilization image signal to the distortion removal unit 34.

In step S5, the distortion removal unit 34 removes rolling shutter distortion from the stabilization image signal received from the image cut-out unit 33, if any, and outputs the resultant stabilization image signal to the image output unit 35. The image output unit 35 outputs the stabilization image signal, which is input via the distortion removal unit 34, to the display device 13.

As described above, the endoscope system 10 according to the present embodiment is capable of correcting a camera shake which may be produced in a video image captured by the endoscope device 11.

Figure 12:
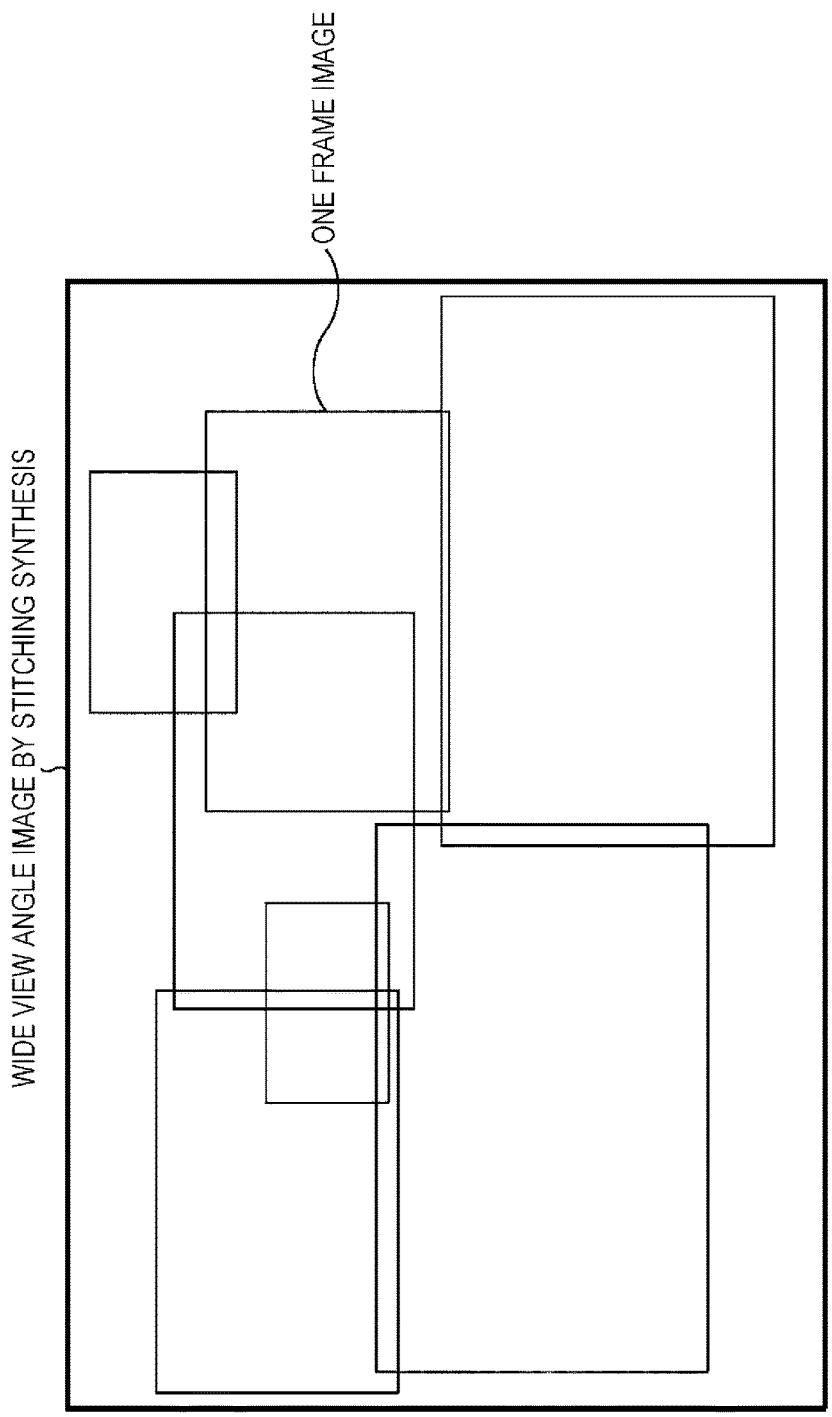
FIG. 12 is a view illustrating stitching-synthesis using images subjected to image stabilization.

Note that, for example, a plurality of images may be obtained by widely moving the endoscope device 11 around the trocar serving as the rotation center, and be synthesized by stitching synthesis based on the position of the rotation sensor and the angular velocity as illustrated in FIG. 12. In this case, a highly accurate and wide view angle image can be obtainable only by a relatively small volume of processing.

According to the method discussed above, successive images formed at positions varied due to camera shakes are aligned and displayed for implementation of image stabilization. This method is also applicable to generation of a single image from a plurality of images by overlapping these images at the same position. When this method is applied, noise removal is achievable.

A shift amount calculated for correcting a camera shake is usable as an index for indicating the degree of a camera shake as well. In this case, a larger shift amount can be considered as a larger degree of a camera shake. Accordingly, the degree of fatigue of a user is measurable based on a shift amount considered as an index indicating the degree of fatigue of the user, for example.

A series of processes carried out by the image correction device 12 described herein may be performed either by hardware or by software. When the series of processes are performed by software, programs included in the software are installed in a computer. Examples of the computer used herein include a computer incorporated in dedicated hardware, and a computer, for example, a general-purpose personal computer, capable of performing various types of functions under various types of programs installed in the computer.

Figure 13:
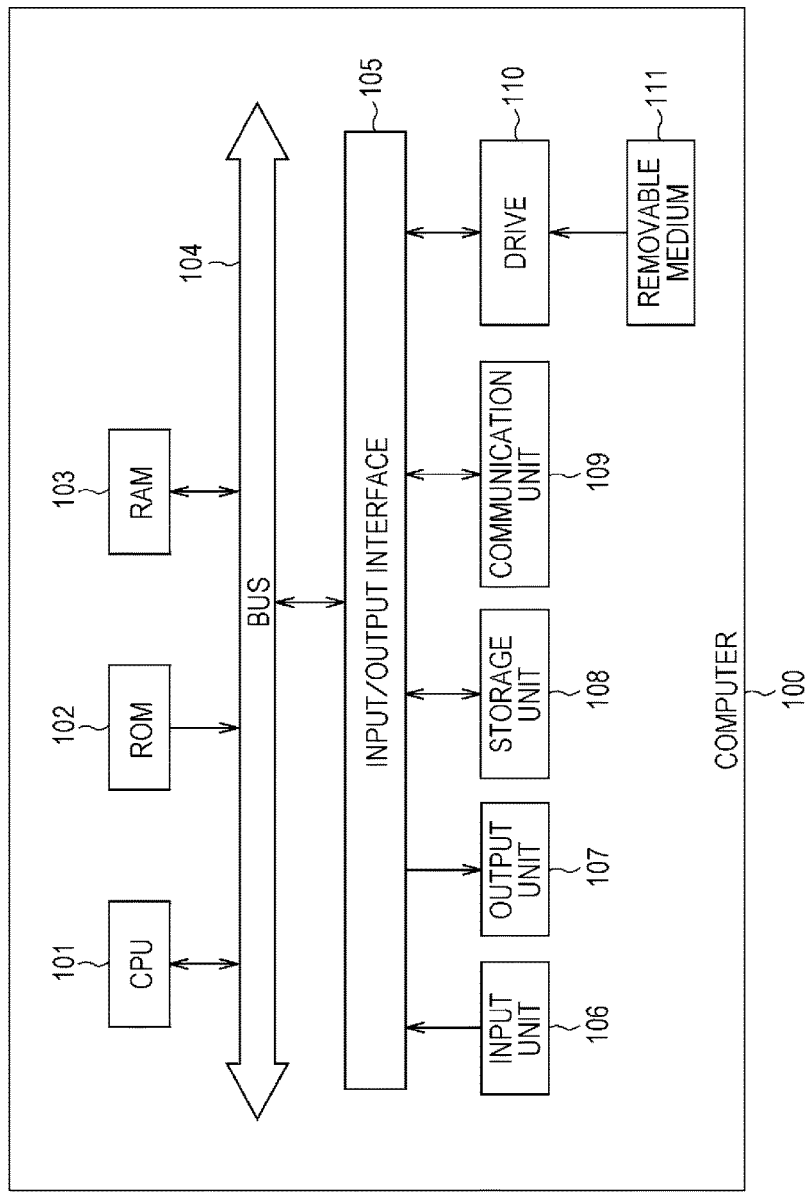
FIG. 13 is a block diagram illustrating a configuration example of a computer.

FIG. 13 is a block diagram illustrating a configuration example of hardware of a computer which performs the series of processes described above under the programs.

A CPU (Central Processing Unit) 101, a ROM (Read Only Memory) 102, and a RAM (Random Access Memory) 103 of a computer 100 are connected with each other via a bus 104.

An input/output interface 105 is further connected with the bus 104. An input unit 106, an output unit 107, a storage unit 108, a communication unit 109, and a drive 110 are connected with the input/output interface 105.

The input unit 106 includes a keyboard, a mouse, a microphone, and others. The output unit 107 includes a display, a speaker, and others. The storage unit 108 includes a hard disk, a non-volatile memory, and others. The communication unit 109 includes a network interface, and others. The drive 110 drives a removable medium 111, such as a magnetic disk, an optical disk, a magneto-optical disk, and a semiconductor memory.

According to the computer 100 having this structure, the CPU 101 performs the series of processes described herein by, for example, loading the programs stored in the storage unit 108 into the RAM 103 via the input/output interface 105 and the bus 104 and executing the loaded programs.

The programs executed by the computer 100 (CPU 101) may be recorded on a removable medium 111 as a package media, or the like, and provided in the form of the removable medium 111, for example. In addition, the programs may be presented via a wired or wireless transmission medium, such as a local area network, the Internet, and digital satellite broadcasting.

The programs executed by the computer 100 may be programs under which processes are performed in time series in the order described herein, or may be programs under which processes are performed in parallel, or at necessary timing such as occasions of calls.

Embodiments of the present technology are not limited to the specific embodiment described herein. Various modifications and changes may be made without departing from the subject matters of the present technology.

The present technology may have the following configurations.

(1) An endoscope system including:
an endoscope device that includes an objective lens provided at a distal end, the objective lens being disposed such that an optical axis of the objective lens and a longitudinal axis of the objective lens intersect at a predetermined angle, an endoscope head provided at a proximal end, and a gyro sensor provided on the endoscope head and to detect an angular velocity of movement of the endoscope head; and image processing circuitry configured to implement image stabilization of an image signal input from the endoscope device based on the detected angular velocity.

(2) The endoscope system according to (1), wherein the endoscope device is an oblique-view endoscope.

(3) The endoscope system according to (2), wherein an oblique-view angle of the oblique-view endoscope is selected from an angle of 30 degrees or an angle of 70 degrees.

(4) The endoscope system according to any one of (1) through (3), wherein the image processing circuitry is configured to measure the oblique-view angle based on the image signal.

(5) The endoscope system according to any one of (1) through (4), wherein the image processing circuitry is configured to level the detected angular velocities in a time direction.

(6) The endoscope system according to any one of (1) through (5), wherein the image processing circuitry is further configured to remove rolling shutter distortion from the image signal having been subjected to image stabilization.

(7) The endoscope system according to (1), wherein the image processing circuitry is further configured to generate wide view angle image based on plurality of images obtained by moving the endoscope device.

(8) The endoscope system according to (1), wherein the image processing circuitry is further configured to measure an index indicating fatigue of a user based on a shift amount.

(9) The endoscope system according to (1), wherein the endoscope device is detachable from the endoscope head and the endoscope head receives scope information transmitted from the endoscope device.

(10) The endoscope system according to (9), wherein the scope information includes an oblique view angle.

(11) The endoscope system according to (9), wherein the scope information includes scope type information.

(12) The endoscope system according to (1), wherein image processing circuitry is further configured to implement the image stabilization of the image signal by cutting out a cut-out area based on the detected angular velocity.

(13) An image processing device for image stabilization of an image signal input from an endoscope device including an objective lens provided at a distal end, the objective lens being disposed such that an optical axis of the objective lens and longitudinal axis of the objective lens intersect a predetermined angle, an endoscope head provided at a proximal end, and a gyro sensor provided on the endoscope head and to detect an angular velocity of movement of the endoscope head, comprising: circuitry configured to implement the image stabilization of the image signal input from the endoscope device based on the angular velocity of movement of the endoscope head of the endoscope device detected by the endoscope device.

(14) An image processing method implemented by image processing circuitry configured to process an image signal input from an endoscope device, the endoscope device including an objective lens provided at a distal end, the objective lens being disposed such that an optical axis of the objective lens and longitudinal axis of the objective lens intersect at a predetermined angle, an endoscope head provided at a proximal end, and a gyro sensor provided on the endoscope head and to detect an angular velocity of movement of the endoscope head, the method including: implementing image stabilization of the image signal based on the detected angular velocity of movement of the endoscope head of the endoscope device.

(15) A non-transitory computer readable medium having stored thereon a program which when executed by a computer causes the computer to implement a method implemented by image processing circuitry configured to process an image signal input from an endoscope device, the endoscope device including an objective lens provided at a distal end, the objective lens being disposed such that an optical axis of the objective lens and longitudinal axis of the objective lens intersect at a predetermined angle, an endoscope head provided at a proximal end, and a gyro sensor provided on the endoscope head and to detect an angular velocity of movement of the endoscope head, the method including: implementing image stabilization of the image signal based on the detected angular velocity of movement of the endoscope head of the endoscope device.

(16) An endoscope system including:
an endoscope device that includes
an objective lens provided at a tip of a rigid insertion portion inserted into a body cavity, the objective lens being disposed such that an optical axis of the objective lens and an axial direction of the insertion portion form a predetermined angle,
a head unit provided at a base end of the insertion portion, and
a gyro unit provided on the head unit to detect an angular velocity of movement of the head unit; and
an image processing device including a correction unit that cuts out a cut-out area, based on the detected angular velocity, from an effective pixel area of an image signal input from the endoscope device and corresponding to an optical image on which light is concentrated by the objective lens, the correction unit implementing image stabilization of the image signal based on the cut-out area.

(17) The endoscope system according to (16), wherein the endoscope device is an oblique-view scope that includes an objective lens whose optical axis and the axial direction of the insertion portion form an oblique-view angle corresponding to a predetermined angle.

(18) The endoscope system according (17), wherein the oblique-view angle includes an angle of 30 degrees and an angle of 70 degrees.

(19) The endoscope system according to any one of (16) through (18), wherein the image processing device measures the oblique-view angle based on the image signal.

(20) The endoscope system according to any one of (16) through (19), wherein the image processing device further includes an angular velocity leveling unit that levels the detected angular velocities in a time direction.

(16) The endoscope system according to any one of (16) through (20), wherein the image processing device further includes a distortion removal unit that removes rolling shutter distortion from the image signal having been subjected to image stabilization.

(22) An image processing device including a correction unit that implements image stabilization of the image signal based on the cut-out area by cutting out a cut-out area, based on an angular velocity of movement of a head unit of an endoscope device detected by the endoscope device, from an effective pixel area of an image signal input from the endoscope device and corresponding to an optical image on which light is concentrated by an objective lens, wherein
the endoscope device includes
the objective lens provided at a tip of a rigid insertion portion inserted into a body cavity, the objective lens being disposed such that an optical axis of the objective lens and an axial direction of the insertion portion form a predetermined angle,
the head unit provided at a base end of the insertion portion, and
a gyro unit provided on the head unit to detect the angular velocity of movement of the head unit.

(23) An image processing method for an image processing device that processes an image signal input from an endoscope device, the endoscope device including
an objective lens provided at a tip of a rigid insertion portion inserted into a body cavity, the objective lens being disposed such that an optical axis of the objective lens and an axial direction of the insertion portion form a predetermined angle,
a head unit provided at a base end of the insertion portion, and
a gyro unit provided on the head unit to detect an angular velocity of movement of the head unit, the method including
implementing image stabilization of the image signal by cutting out a cut-out area, based on the detected angular velocity of movement of the head unit of the endoscope device, from an effective pixel area of the image signal corresponding to an optical image on which light is concentrated by the objective lens.

(24) A program under which a computer controls an image processing device that processes an image signal input from an endoscope device and corresponding to an optical image on which light is concentrated by an objective lens, the endoscope device including
the objective lens provided at a tip of a rigid insertion portion inserted into a body cavity, the objective lens being disposed such that an optical axis of the objective lens and an axial direction of the insertion portion form a predetermined angle,
a head unit provided at a base end of the insertion portion, and
a gyro unit provided on the head unit to detect an angular velocity of movement of the head unit, and
the program the computer functioning as a correction unit that cuts out a cut-out area, based on the detected angular velocity, from an effective pixel area of the image signal corresponding to the optical image on which light is concentrated by the objective lens, the correction unit implementing image stabilization of the image signal based on the cut-out area.

REFERENCE SIGNS LIST 2 trocar
10 endoscope system
11 endoscope device
12 image correction device
13 display device
14 light source device
21 barrel unit
22 objective lens
23 optical lens unit
24 head unit
25 imaging unit
26 gyro unit
31 angular velocity leveling unit
32 shift amount determination unit
33 image cut-out unit
34 distortion removal unit
35 image output unit
100 computer
101 CPU

The invention claimed is:

1. An endoscope system comprising:
an endoscope device that includes
an objective lens provided at a distal end, the objective lens being disposed such that an optical axis of the objective lens and a longitudinal axis of the objective lens intersect at a predetermined angle,
an endoscope head provided at a proximal end, and
a gyro sensor provided on the endoscope head and configured to detect an angular velocity of movement of the endoscope head; and
image processing circuitry configured to
calculate a shift amount of the distal end of the endoscope device using the detected angular velocity of movement of the endoscope head provided at the proximal end, and
implement image stabilization of an image signal input from the endoscope device based on the calculated shift amount of the distal end of the endoscope device.

2. The endoscope system according to claim 1, wherein the endoscope device is an oblique-view endoscope.

3. The endoscope system according to claim 2, wherein an oblique-view angle of the oblique-view endoscope is selected from an angle of 30 degrees or an angle of 70 degrees.

4. The endoscope system according to claim 1, wherein the image processing circuitry is configured to measure the oblique-view angle based on the image signal.

5. The endoscope system according to claim 1, wherein the image processing circuitry is configured to level detected angular velocities in a time direction.

6. The endoscope system according to claim 1, wherein the image processing circuitry is further configured to remove rolling shutter distortion from the image signal having been subjected to image stabilization.

7. The endoscope system according to claim 1, wherein the image processing circuitry is further configured to generate wide view angle image based on plurality of images obtained by moving the endoscope device.

8. The endoscope system according to claim 1, wherein the image processing circuitry is further configured to measure an index indicating fatigue of a user based on the shift amount.

9. The endoscope system according to claim 1, wherein the endoscope device is detachable from the endoscope head and the endoscope head receives scope information transmitted from the endoscope device.

10. The endoscope system according to claim 9, wherein the scope information includes an oblique view angle.

11. The endoscope system according to claim 9, wherein the scope information includes scope type information.

12. The endoscope system according to claim 1, wherein image processing circuitry is further configured to implement the image stabilization of the image signal by cutting out a cut-out area based on the detected angular velocity.

13. An image processing device for image stabilization of an image signal input from an endoscope device including an objective lens provided at a distal end, the objective lens being disposed such that an optical axis of the objective lens and longitudinal axis of the objective lens intersect a predetermined angle, an endoscope head provided at a proximal end, and a gyro sensor provided on the endoscope head and configured to detect an angular velocity of movement of the endoscope head, image processing device comprising:
circuitry configured to
calculate a shift amount of the distal end of the endoscope device using the detected angular velocity of movement of the endoscope head provided at the proximal end, and
implement the image stabilization of the image signal input from the endoscope device based on the calculated shift amount of the distal end of the endoscope device.

14. An image processing method implemented by image processing circuitry configured to process an image signal input from an endoscope device, the endoscope device including an objective lens provided at a distal end, the objective lens being disposed such that an optical axis of the objective lens and longitudinal axis of the objective lens intersect at a predetermined angle, an endoscope head provided at a proximal end, and a gyro sensor provided on the endoscope head and configured to detect an angular velocity of movement of the endoscope head, the method comprising:
calculating a shift amount of the distal end of the endoscope device using the detected angular velocity of movement of the endoscope head provided at the proximal end; and
implementing image stabilization of the image signal based on the calculated shift amount of the distal end of the endoscope device.

15. A non-transitory computer readable medium having stored thereon a program which when executed by a computer causes the computer to implement a method implemented by image processing circuitry configured to process an image signal input from an endoscope device, the endoscope device including an objective lens provided at a distal end, the objective lens being disposed such that an optical axis of the objective lens and longitudinal axis of the objective lens intersect at a predetermined angle, an endoscope head provided at a proximal end, and a gyro sensor provided on the endoscope head and configured to detect an angular velocity of movement of the endoscope head, the method comprising:
calculating a shift amount of the distal end of the endoscope device using the detected angular velocity of movement of the endoscope head provided at the proximal end; and
implementing image stabilization of the image signal based on the calculated shift amount of the distal end of the endoscope device.

* * * * *